United States Patent [19]

Jäger et al.

[11] Patent Number: 4,917,720
[45] Date of Patent: Apr. 17, 1990

[54] FUNGICIDAL AND PLANT-GROWTH REGULATING AZOLYL ETHER KETONES AND ALCOHOLS

[75] Inventors: Gerhard Jäger, Leverkusen; Manfred Jautelat, Burscheid; Wolfgang Krämer, Burscheid; Karl H. Büchel, Burscheid; Paul Reinecke, Leverkusen; Wilhelm Brandes, Leichlingen; Gerd Hänssler, Leverkusen; Klaus Lürssen, Gladbach, all of Fed. Rep. of Germany

[73] Assignee: Bayer Aktiengesellschaft, Leverkusen, Fed. Rep. of Germany

[21] Appl. No.: 256,808

[22] Filed: Oct. 12, 1988

Related U.S. Application Data

[62] Division of Ser. No. 930,634, Nov. 13, 1986, abandoned.

[30] Foreign Application Priority Data

Nov. 15, 1985 [DE] Fed. Rep. of Germany ....... 3540523

[51] Int. Cl.$^4$ .................. A01N 43/653; C07D 249/08
[52] U.S. Cl. .......................................... 71/92; 71/76; 514/184; 514/383; 548/101; 548/268.2
[58] Field of Search ................ 548/101, 262; 514/184, 514/383; 71/76, 92

[56] References Cited

U.S. PATENT DOCUMENTS

| | | | |
|---|---|---|---|
| 3,912,752 | 10/1975 | Meiser et al. | 548/262 |
| 3,952,002 | 4/1976 | Kramer et al. | 548/262 |
| 4,255,434 | 3/1981 | Kramer et al. | 548/262 |
| 4,507,140 | 3/1985 | Sugananom | 548/101 |
| 4,507,141 | 3/1985 | Regel et al. | 548/101 |
| 4,549,900 | 10/1985 | Kramer et al. | 71/92 |
| 4,711,657 | 12/1987 | Kramer et al. | 548/262 |

FOREIGN PATENT DOCUMENTS

| | | | |
|---|---|---|---|
| 2632601 | 1/1978 | Fed. Rep. of Germany | 548/262 |
| 2811919 | 9/1979 | Fed. Rep. of Germany | 548/262 |
| 2842137 | 4/1980 | Fed. Rep. of Germany | 548/262 |

OTHER PUBLICATIONS

Phytopathology 33, 1113, (1963).
Chemical Abstracts, Band 93, Nr. 15, 13, Oct. 1980, Columbus, OH, U.S.A. Nishiyama, Ryuzo; Haga, Takahirol Komyoji, Termumasa (Ishihara Sangyo Kaisha, Lt), "Pyridyloxyalkylazoles", Seite 720, Spalte 2, Zusammenfassung Nr. 150 257y & Jpn. Kokai Tokyo Koho 80 28,923.

*Primary Examiner*—Richard L. Raymond
*Assistant Examiner*—Patricia L. Morris
*Attorney, Agent, or Firm*—Sprung Horn Kramer & Woods

[57] ABSTRACT

Azolyl ether ketones and alcohols of the formula $$R^2-\underset{\underset{R^3}{|}}{\overset{\overset{R^1}{|}}{C}}-A-\underset{\underset{\substack{N \\ \diagdown \\ N\diagdown_{Z} \\ \diagup\!\!\!\!\diagup}}{|}}{CH}-X-Ar$$

in which
R$^1$ and R$^2$ each independently represents alkyl with more than one carbon atom, or
R$^1$ represents dichloromethyl, trichloromethyl, chlorovinyl or dichlorovinyl, and
R$^2$ represents alkyl,
R$^3$ represents alkyl,
A represents the keto group or a CH(OH) grouping,
Z represents a nitrogen atom or the CH group,
X represents oxygen or sulfur and
Ar represents optionally substituted phenyl, or addition products thereof with acids and metal salts, are active against fungi and in regulating the growth of plants. New intermediates therefor are also shown.

8 Claims, No Drawings

FUNGICIDAL AND PLANT-GROWTH REGULATING AZOLYL ETHER KETONES AND ALCOHOLS

This application is a division of application Ser. No. 930,634, filed Nov. 13, 1986, now abandoned.

The present invention relates to new azolyl ether ketones and alcohols, several processes for their preparation and their use as fungicides and plant growth regulators.

It is already known that numerous azolyl ether ketones and alcohols have fungicidal and plant growth-regulating properties (compare DE-OS (German Published Specification) 2,632,603, DE-OS (German Published Specification) 2,333,355, DE-OS (German Published Specification) 2,325,156, DE-OS (German Published Specification) 2,234,010 and DE-OS (German Published Specification) 2,105,490). Thus, for example, 4-chloro-3,3-dimethyl-1-(2,4-dichlorophenoxy)-1-(1,2,4-triazol-1-yl)-butan-2-one, 3,3-dimethyl-1-(4-fluorophenoxy)-1-(1,2,4-triazol-1-yl)-butanol, 3,3-dimethyl-1-(2,4-dichlorophenoxy)-1-(1,2,4-triazol-1-yl)-butan-2-one, 3,3-dimethyl-1-(4-fluorophenoxy)-1-(imidazol-1-yl)-butan-2-ol, 4-chloro-1-(4-chlorophenoxy)-3,3-dimethyl-1-(1,2,4-triazol-1-yl)-butan-2-one, 3,3-dimethyl-1-(2,4-dichlorophenoxy)-1-(1,2,4-triazol-1-yl)-butan-2-ol, 1-(4-chlorophenoxy)-3,3-dimethyl-1-(triazol-1-yl)-butan-2-ol, 1-(4-(biphenoxy)-4-chloro-3,3-dimethyl-1-(imidazol-1-yl)-butan-2-one and 1-(4-biphenoxy)-3,3-dimethyl-1-(imidazol-1-yl)-butan-2-ol can be used as fungicides. However, the activity of these substances is not always satisfactory, especially when low amounts are applied.

It has furthermore already been disclosed that zinc ethylene-1,2-bisdithiocarbamidate can be used particularly readily for combating fungal plant diseases (compare Phytopathology 33, 1113 (1963)). The use of this substance is limited, however, by the fact that the action is not always sufficient at low dosages.

New azolyl ether ketones and alcohols of the formula (I)

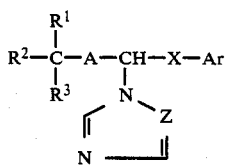

in which
$R^1$ represents alkyl with more than one carbon atom,
$R^2$ represents alkyl with more than one carbon atom,
$R^3$ represents alkyl,
A represents the keto group or a CH(OH) grouping,
Z represents a nitrogen atom or the CH group,
X represents oxygen or sulphur and
Ar represents optionally substituted phenyl, or
$R^1$ represents dichloromethyl, trichloromethyl, chlorovinyl or dichlorovinyl,
$R^2$ represents alkyl,
$R^3$ represents alkyl,
A represents the keto group or a CH(OH) grouping,
Z represents a nitrogen atom or the CH group,
X represents oxygen or sulphur and
Ar represents optionally substituted phenyl, and acid addition salts and metal salt complexes thereof, have now been found.

The compounds of the formula (I) in which A represents a keto group have at least one asymmetrically substituted carbon atom, and the compounds of the formula (I) in which A represents the CH(OH) group have at least two asymmetrically substituted carbon atoms. The compounds of the formula (I) can therefore exist in various optical isomer forms, which can be obtained in different proportions. Those compounds of the formula (I) in which $R^1$, $R^2$ and $R^3$ are different contains an additional asymmetrically substituted carbon atom, further optical isomers resulting. The invention relates both to racemates and to the individual isomers and mixtures thereof.

It has furthermore been found that the new azolyl ether ketones and alcohols of the formula (I) and acid addition salts and metal salt complexes thereof are obtained by a process in which (a) halogenoether ketones of the formula (II)

in which
$R^1$, $R^2$, $R^3$, X and Ar have the abovementioned meanings and
Hal represents halogen,
are reacted with 1,2,4-triazole or imidazole, if appropriate in the presence of an acid-binding agent and if appropriate in the presence of a diluent, and, if appropriate, (b) the azolyl ether ketones obtained by process (a), of the formula (Ia)

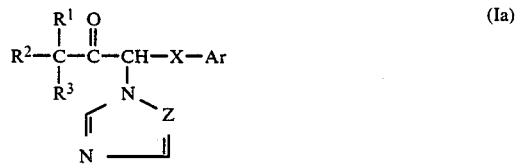

in which
$R^1$, $R^2$, $R^3$, Z, X and Ar have the abovementioned meanings,
are reduced, if appropriate in the presence of a diluent, and, if appropriate, an acid or a metal salt is then added on.

Finally, it has been found that the new azolyl ether ketones and alcohols of the formula (I) and acid addition salts and metal salt complexes thereof have very good fungicidal and plant growth-regulating properties.

Surprisingly, the substances according to the invention exhibit a considerably better fungicidal and plant growth-regulating action than the substances 4-chloro-3,3-dimethyl 1-(2,4-dichlorophenoxy)-1-(1,2,4-triazol-1-yl)-butan-2-one, 3,3-dimethyl-1-(4-fluorophenoxy)-1-(1,2,4-triazol-1-yl)-butan-2-ol, 3,3-dimethyl-1-(2,4-dichlorophenoxy)-1-(1,2,4-triazol-1-yl)-butan-2-one, 3,3-dimethyl-1-(4-fluorophenoxy)-1-(imidazol-1-yl)-butanol, 4-chloro-1-(4-chlorophenoxy)-3,3-dimethyl-1-(1,2,4-triazol-1-yl)-butan-2-one, 3,3-dimethyl-1-(2,4-dichlorophenoxy)-1-(1,2,4-triazol-1-yl)-butan-2-ol, 1-(4-chlorophenoxy)-3,3-dimethyl-1-(triazol-1-yl)-butan-2-ol, 1-(4-biphenoxy)-4-chloro-3,3-dimethyl-1-(imidazol- 1-yl)-butan-2-one and 1-(4-biphenoxy)-3,3-dimethyl-1-(imidazol-1-yl)-butan-2-ol, which are known from the prior art and are closely related compounds structurally and from the point of view of their action. The substances according to the invention also have a better fungicidal action than zinc ethylene-1,2-bis-dithiocarbamidate, which is already known from the prior art and is a closely related compound from the point of view of its action.

Formula (I) provides a general definition of the azolyl ether ketones and alcohols according to the invention. Preferably, in this formula, $R^1$ represents straight-chain or branched alkyl with 2 to 6 carbon atoms, $R^2$ represents straight-chain or branched alkyl with 2 to 6 carbon atoms, $R^3$ represents straight-chain or branched alkyl with 1 to 6 carbon atoms, A represents the keto group or a CH(OH) grouping, Z represents oxygen or sulphur and Ar represents phenyl which is optionally mono-, di-, tri- or tetrasubstituted by identical or different substituents, preferred possible substituents being: halogen, alkyl with 1 to 4 carbon atoms, halogenoalkyl with 1 or 2 carbon atoms and 1 to 5 identical or different halogen atoms, such as fluorine and chlorine, alkoxy and alkylthio with in each case 1 to 4 carbon atoms, alkoximinomethyl with 1 to 6 carbon atoms in the alkoxy part and phenyl which is optionally mono-, di- or trisubstituted by identical or different substituents, possible substituents being fluorine, chlorine, methyl and trifluoromethyl, or, preferably, $R^1$ represents dichloromethyl, trichloromethyl, chlorovinyl or dichlorovinyl, $R^2$ represents straight-chain or branched alkyl with 1 to 6 carbon atoms, $R^3$ represents straight-chain or branched alkyl with 1 to 6 carbon atoms, A represents the keto group or a CH(OH) grouping, Z represents oxygen or sulphur and Ar represents phenyl which is optionally mono-, di-, tri- or tetrasubstituted by identical or different substituents, preferred possible substituents being: halogen, alkyl with 1 to 4 carbon atoms, halogenoalkyl with 1 or 2 carbon atoms and 1 to 5 identical or different halogen atoms, such as fluorine and chlorine, alkoxy and alkylthio with in each case 1 to 4 carbon atoms, alkoximinomethyl with 1 to 6 carbon atoms in the alkoxy part and phenyl which is optionally mono-, di- or tri- substituted by identical or different substituents, possible substituents being fluorine, chlorine, methyl and trifluoromethyl.

Particularly preferred compounds of the formula (I) are those in which $R^1$ represents straight-chain or branched alkyl with 2 to 4 carbon atoms, $R^2$ represents straight-chain or branched alkyl with 2 to 4 carbon atoms, $R^3$ represents straight-chain or branched alkyl with 1 to 4 carbon atoms, A represents the keto group or a CH(OH) group, Z represents a nitrogen atom or the CH group, X represents oxygen or sulphur and Ar represents phenyl which is optionally mono-, di- or trisubstituted by identical or different substituents, substituents which may be mentioned being, in particular: fluorine, chlorine, bromine, iodine, methyl, ethyl, isopropyl, trifluoromethyl, methoxy, ethoxy, isopropoxy, methylthio, ethylthio, isopropylthio, alkoximinomethyl with 1 to 4 carbon atoms in the alkoxy part and phenyl which is optionally mono- or disubstituted by identical or different substituents, possible substituents being fluorine, chlorine, methyl and trifluoromethyl.

Particularly preferred compounds of the formula (I) are also those in which $R^1$ represents dichloromethyl, trichloromethyl, chlorovinyl or dichlorovinyl, $R^2$ represents straight-chain or branched alkyl with 1 to 4 carbon atoms and $R^3$ represents straight-chain or branched alkyl with 1 to 4 carbon atoms, A represents the keto groups or a CH(OH) group, Z represents a nitrogen atom or the CH group, X represents oxygen or sulphur and Ar represents phenyl which is optionally mono-, di- or trisubstituted by identical or different substituents, substituents which may be mentioned being, in particular: fluorine, chlorine, bromine, iodine, methyl, ethyl, isopropyl, trifluoromethyl, methoxy, ethoxy, isopropoxy, methylthio, ethylthio, isopropylthio, alkoximinomethyl with 1 to 4 carbon atoms in the alkoxy part and phenyl which is optionally mono- or disubstituted by identical or different substituents, possible substituents being fluorine, chlorine, methyl and trifluoromethyl.

Addition products of acids and those azolyl ether ketones and alcohols of the formula (I) in which the substituents $R^1$, $R^2$, $R^3$, A, Z, X and Ar have the meanings which have already been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenedisulphonic acid.

Addition products of salts of metals of main group II to IV and sub-group I and II and IV to VIII of the periodic table of the elements and those substituted azolyl ether ketones and alcohols of the formula (I) in which the substituents $R^1$, $R^2$, $R^3$, A, X, Z and Ar have the meanings which have already been mentioned as preferred for these substituents are furthermore preferred compounds according to the invention.

Salts of copper, zinc, manganese, magnesium, tin, iron and nickel are particularly preferred here. Possible anions of these salts are those which are derived from acids which lead to physiologically acceptable addition products. Particularly preferred acids of this type are, in this connection, the hydrogen halide acids, such as, for example, hydrochloric acid and hydrobromic acid, and furthermore phosphoric acid, nitric acid and sulphuric acid.

The following compounds of the formula (I) may be mentioned specifically, in addition to the compounds mentioned in the preparation examples:

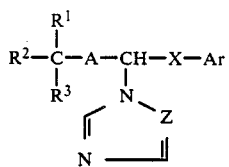

(I)

| R¹ | R² | R³ | A | Z | X | Ar |
|---|---|---|---|---|---|---|
| CHCl₂ | CH₃ | CH₃ | CO | N | O | 4-F-C₆H₄ |
| CHCl₂ | CH₃ | CH₃ | CO | CH | O | 4-F-C₆H₄ |
| CHCl₂ | CH₃ | CH₃ | CHOH | N | O | 4-F-C₆H₄ |
| CHCl₂ | CH₃ | CH₃ | CHOH | CH | O | 4-F-C₆H₄ |
| CHCl₂ | CH₃ | CH₃ | CO | N | S | 4-Cl-C₆H₄ |
| CHCl₂ | CH₃ | CH₃ | CHOH | N | S | 4-Cl-C₆H₄ |
| CHCl₂ | CH₃ | CH₃ | CO | N | O | 4-Cl-3-CH₃-C₆H₃ |
| CHCl₂ | CH₃ | CH₃ | CHOH | N | O | 4-Cl-3-CH₃-C₆H₃ |
| CHCl₂ | CH₃ | CH₃ | CO | N | O | 4-Br-C₆H₄ |
| CHCl₂ | CH₃ | CH₃ | CO | CH | O | 4-Br-C₆H₄ |
| CHCl₂ | CH₃ | CH₃ | CHOH | N | O | 4-Br-C₆H₄ |
| CHCl₂ | CH₃ | CH₃ | CHOH | CH | O | 4-Br-C₆H₄ |
| n-C₄H₉ | C₂H₅ | CH₃ | CO | N | O | 4-Br-C₆H₄ |
| n-C₄H₉ | C₂H₅ | CH₃ | CO | N | O | 4-Br-C₆H₄ |
| n-C₄H₉ | C₂H₅ | CH₃ | CHOH | N | O | 4-Br-C₆H₄ |
| n-C₄H₉ | C₂H₅ | CH₃ | CO | N | O | 4-Cl-3-CH₃-C₆H₃ |
| n-C₄H₉ | C₂H₅ | CH₃ | CO | CH | O | 4-Cl-3-CH₃-C₆H₃ |
| C₂H₅ | C₂H₅ | CH₃ | CO | N | O | 4-C₆H₅-C₆H₄ |
| C₂H₅ | C₂H₅ | CH₃ | CO | CH | O | 4-C₆H₅-C₆H₄ |
| C₂H₅ | C₂H₅ | CH₃ | CHOH | N | O | 4-C₆H₅-C₆H₄ |
| C₂H₅ | C₂H₅ | CH₃ | CHOH | CH | O | 4-C₆H₅-C₆H₄ |
| C₂H₅ | C₂H₅ | CH₃ | CO | N | O | 4-F-C₆H₄ |
| C₂H₅ | C₂H₅ | CH₃ | CO | CH | O | 4-F-C₆H₄ |
| C₂H₅ | C₂H₅ | CH₃ | CHOH | N | O | 4-F-C₆H₄ |
| C₂H₅ | C₂H₅ | CH₃ | CO | N | O | 4-Br-C₆H₄ |
| C₂H₅ | C₂H₅ | CH₃ | CO | CH | O | 4-Br-C₆H₄ |
| C₂H₅ | C₂H₅ | CH₃ | CO | CH | O | 4-Cl-3-CH₃-C₆H₃ |
| C₂H₅ | C₂H₅ | CH₃ | CO | N | O | 4-Cl-3-CH₃-C₆H₃ |
| C₂H₅ | C₂H₅ | C₂H₅ | CO | N | O | 4-Cl-C₆H₄ |
| C₂H₅ | C₂H₅ | C₂H₅ | CO | CH | O | 4-Cl-C₆H₄ |
| C₂H₅ | C₂H₅ | C₂H₅ | CHOH | N | O | 4-Cl-C₆H₄ |
| C₂H₅ | C₂H₅ | C₂H₅ | CHOH | CH | O | 4-Cl-C₆H₄ |
| ClHC=CH— | CH₃ | CH₃ | CO | N | O | 4-Cl-C₆H₄ |
| ClHC=CH— | CH₃ | CH₃ | CO | CH | O | 4-Cl-C₆H₄ |
| ClHC=CH— | CH₃ | CH₃ | CO | N | O | 3-Cl-4-Cl-C₆H₃ |
| ClHC=CH— | CH₃ | CH₃ | CO | N | O | 4-C₆H₅-C₆H₄ |
| ClHC=CH— | CH₃ | CH₃ | CO | N | O | 4-F-C₆H₄ |
| ClHC=CH— | CH₃ | CH₃ | CHOH | N | O | 4-F-C₆H₄ |
| Cl₂C=CH— | CH₃ | CH₃ | CO | N | O | 4-Cl-C₆H₄ |
| Cl₂C=CH— | CH₃ | CH₃ | CO | CH | O | 4-Cl-C₆H₄ |
| Cl₂C=CH— | CH₃ | CH₃ | CO | N | O | 4-Cl-C₆H₄ |
| Cl₂C=CH— | CH₃ | CH₃ | CHOH | N | O | 2,4-Cl₂-C₆H₃ |

If, for example, 1-bromo-1-(2,4-dichlorophenoxy)-3-ethyl-3-methyl-pentan-2-one and 1,2,4-triazole are used as starting substances, the course of process (a) according to the invention can be represented by the following equation:

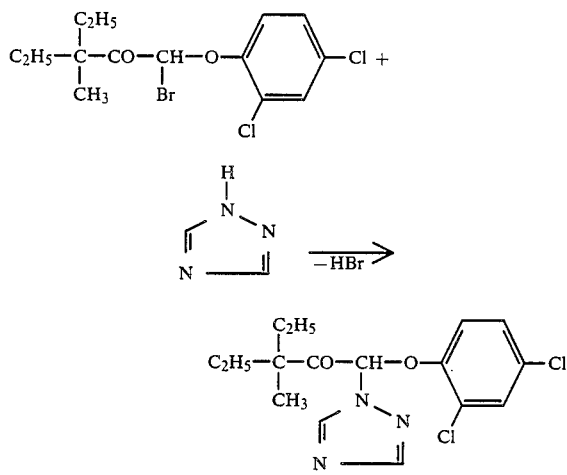

If, for example, 4,4-dichloro-1-(2,4-dichlorophenoxy)-3,3-dimethyl-1-(1,2,4-triazol-1-yl)-butan-2-one is used as the starting substance and sodium borohydride is used as the reducing agent, the course of process (b) according to the invention can be represented by the following equation:

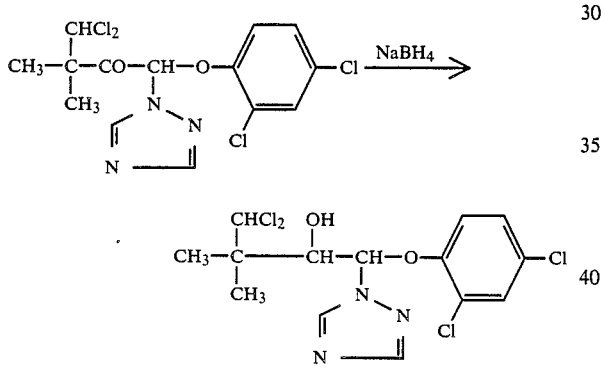

Formula (II) provides a general definition of the halogenoether ketones to be used as starting substances for process (a) according to the invention. In this formula, $R^1$, $R^2$, $R^3$, X and Ar preferably represent the radicals which have already been mentioned as preferred for these substituents in connection with the description of the substances of the formula (I) according to the invention. Hal preferably represents chlorine or bromine.

The halogenoether ketones of the formula (II) are not yet known; however, they can be obtained in a generally known manner, by a process in which, for example, ether ketones of the formula (III)

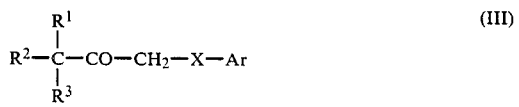

in which
$R^1$, $R^2$, $R^3$, X and Ar have the abovementioned meanings,
are halogenated with a halogenating agent, such as, for example, bromine, sulphuryl chloride or N-bromosuccinimide, in the presence of a solvent, such as, for example, methylene chloride, chloroform, carbon tetrachloride, toluene or chlorobenzene, at temperatures between 0° and 100° C., preferably between 10° and 80° C. If appropriate, the halogenoether ketones formed, of the formula (II), can be further reacted without isolation.

The ether ketones of the formula (III) are likewise not yet known; however, they can be obtained in a generally known manner, by a process in which halogenoketones of the formula (IV)

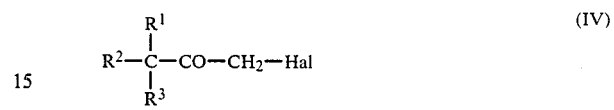

in which
$R^1$, $R^2$, $R^3$ and Hal have the abovementioned meanings,
are reacted with phenols or thiophenols of the formula (V)

in which
Ar and X have the abovementioned meanings, in the presence of a strong base, such as, for example, potassium carbonate or sodium carbonate or triethylamine, and in the presence of an inert organic solvent, such as, for example, N,N-dimethylformamide, acetone, methyl isopropyl ketone or acetonitrile, at temperatures between 50° and 150° C., preferably between 80° and 120° C.

The phenols and thiophenols of the formula (V) are generally known compounds of organic chemistry.

The halogenoketones of the formula (IV) are not yet known; they can be obtained by a process in which, for example, compounds of the general formula (VI)

in which
$R^1$, $R^2$ and $R^3$ have the abovementioned meanings, are hydrolyzed in the presence of an acid, such as, for example, a mineral acid, preferably sulphuric acid or hydrochloric acid, and/or an organic acid, such as formic acid, trifluoroacetic acid, oxalic acid, p-toluenesulphonic acid or methanesulphonic acid, which can also be in the form of an aqueous dilution, at temperatures between 20° and 150° C., preferably between 40° and 100° C., in the presence of a diluent, such as, for example, methanol, ethanol, acetone, methylene chloride or dioxane; (compare DE-OS (German Published Specification) 3,049,461 and the preparation examples).

The compounds of the formula (VI) are not yet known; they can be obtained by a process in which, for example 1,1-dichloroalkenes of the general formula (VII)

in which $R^1$, $R^2$ and $R^3$ have the abovementioned meanings, are reacted with phenolates, such as, for example, sodium phenolate or potassium phenolate, in the presence of a diluent, such as, for example, dimethylformamide, N-methylpyrrolidone, dimethylsulphoxide, 1,1-dimethyl-2-imidazolidone or tetramethylurea, at temperatures between 50° and 250° C. (compare DE-OS (German Published Specification) 3,049,461).

The 1,1-dichloroalkenes of the formula (VII) are not yet known; however, they can be obtained in a generally known manner, by a process in which, for example, chlorine compounds of the formula (VIII)

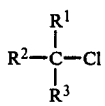

(VIII)

in which $R^1$, $R^2$ and $R^3$ have the abovementioned meanings, are reacted with 1,1-dichloroethane in the presence of metal halides, such as, for example, iron(III) chloride, aluminum (III) chloride or bismuth(III) chloride, at temperatures between −78° and 50° C.

The chlorine compounds of the formula (VIII) are generally known compounds of organic chemistry.

The 1,2,4-triazole to be used as a starting substance for process (a) according to the invention and the imidazole to be used as a starting substance are generally known compounds of organic chemistry.

The azolyl ether ketones of the formula (Ia) to be used as starting substances for carrying out process (b) according to the invention are compounds according to the invention and can be prepared by process (a) according to the invention.

Process (a) according to the invention is preferably carried out in the presence of an inert organic solvent. Solvents which can preferably be used are nitriles, such as propionitrile and in particular acetonitrile; formamides, such as, in particular, dimethylformamide; ketones, such as diethyl ketone, acetone and methyl ethyl ketone; alcohols, such as ethanol and isopropanol; ethers, such as tetrahydrofuran and dioxane; aromatic hydrocarbons, such as benzene and toluene, and halogenated hydrocarbons, such as methylene chloride.

The reaction according to the invention in process (a) is preferably carried out in the presence of an acid-binding agent. All the inorganic or organic acid-binding agents which can usually be employed may be added, such as alkali metal carbonates, for example sodium carbonate, potassium carbonate and sodium bicarbonate, or lower tertiary alkylamines, cycloalkylamines or, aralkylamines, for example triethylamine, N,N-dimethylcyclohexylamine, dicyclohexylamine and N,N-dimethylbenzylamine, and furthermore pyridine and diazabicyclooctane. Preferably, a corresponding excess of 1,2,4-triazole or imidazole is used.

The reaction temperatures can be varied within a substantial range in process (a). The reaction is in general carried out between 20° and 150° C., preferably between 60° and 120° C. If a solvent is present, the reaction is advantageously carried out at the boiling point of the particular solvent.

In carrying out process (a) according to the invention, 1 to 2 moles of 1,2,4-triazole or imidazole and 1 to 2 moles of acid-binding agent are preferably employed per mole of the compounds of the formula (II). To isolate the compounds of the formula (I), the solvent is in general distilled off, the residue is taken up in an organic solvent and the mixture is washed with water. The organic phase is dried over sodium sulphate and freed from the solvent in vacuo. The residue is purified by distillation or recrystallization or salt formation and recrystallization. Other methods of working up can furthermore also be carried out.

The reduction according to the invention in process (b) is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, such as methanol, ethanol, butanol and isopropanol, and ethers, such as diethyl ether or tetrahydrofuran. The reaction is in general carried out at −10° to +30° C., preferably at 0° to 20° C. For the reaction, about 1 mole of a complex hydride, such as sodium borohydride or lithium alanate, is employed per mole of the ketone of the formula (Ia). To isolate the reduced compounds of the formula (I), the residue is in general taken up in dilute hydrochloric acid and the mixture is then rendered alkaline and extracted with an organic solvent. Further working up is carried out in the customary manner.

If aluminum isopropylate is used, preferred possible diluents for the reaction according to the invention are alcohols, such as isopropanol, or inert hydrocarbons, such as benzene. The reaction temperature can again be varied within a substantial range; the reaction is in general carried out between 20° and 120° C., preferably between 50° and 100° C. For carrying out the reaction, about 0.3 to 2 moles of aluminum isopropylate are employed per mole of a ketone of the formula (Ia). To isolate the reduced compounds of the formula (I), the excess solvent is in general removed in vacuo and the aluminum compounds formed are decomposed with dilute aqueous sulphuric acid or sodium hydroxide solution. Further working up is carried out in the customary manner.

Those acids which have already been mentioned as preferred acids in connection with the description of the acid addition salts according to the invention can preferably be used in the preparation of acid addition salts of the compounds of the formula (I).

The acid addition salts of the compounds of the formula () can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above can preferably be used for the preparation of the metal salt complexes of the compounds of the general formula (I).

The metal salt complexes of compounds of the general formula (I) can be obtained in a simple manner by customary processes, for example by dissolving the metal salt in alcohol, for example ethanol, and adding the solution to compounds of the general formula (I). The metal salt complexes can be isolated in a known manner, for example by filtration, and if appropriate can be purified by recrystallization.

The active compounds according to the invention exhibit a powerful microbicidal action and can be employed in practice for combating undesirable microorganisms. The active compounds are suitable for use as plant protection agents.

Fungicidal agents in plant protection are employed for combating Plasmodiophoromycetes, Oomycete, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as, for example, Xanthomonas oryzae; Pseudomonas species, such as, for example, *Pseudomonas lachrymans;* Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea;* (conidia form: Drechslera, syn: Helminthosporium); Cochliobolus species, such as, for example, *Cochliobolus sativus;* (conidia form: Drechslera, syn: Helminthosporium); Uromyces species, such as, for example, *Uromyces appendiculatus;* Puccinia species, such as, for example, Puccinia recondita; Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fosarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Puccinia species, such as *Puccinia recondita,* and leptosphaeria species, such as *Leptosphaeria nodorum* or wheat; and furthermore for combating Sphaerotheca species, such as *Sphaerotheca fuliginea* on cucumbers, Venturia species, such as *Venturia inequalis* on apples, Uromyces species, such as *Uromyces appendiculatus* on dwarf beans, and also for combating *Pyricularia oryzae* on rice. The active compounds according to the invention are furthermore particularly suitable for combating mildew and *Cochiobolus sativus* and *Pyrenophora teres* on cereals.

The active compounds according to the invention also have plant growth-regulating properties.

The active compounds according to the invention engage in the metabolism of the plants and can therefore be employed as growth regulators.

Experience to data of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating compounds can be employed, for example, to inhibit vegetative growth of the plants. Such inhibition of growth is, inter alia, of economic interest in the case of grasses, since it is thereby possible to reduce the frequency of cutting the grass in ornamental gardens, parks and sportsground, at verges, at airports or in fruit orchards. The inhibition of growth of herbaceous and woody plants at verges and in the vicinity of pipelines or overland lines or, quite generally, in areas in which heavy additional growth of plants is undesired, is also of importance.

The use of growth regulators to inhibit the growth in length of cereals is also important. The danger of bending ("Lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soy beans or cereals. Using growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great imortance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquid which are gaseous at normal temperature and under normal pressure, for example aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysis products; as dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulation or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore it is possible to apply the active compounds in accordance with the ultra-low volume process or to inject the active compound preparation or the active compound itself into the soil. It is also possible to treat the seeds of plants.

When the substances according to the invention are used as fungicides, the amount applied can be varied within a substantial range, depending on the type of application. Thus, in the treatment of parts of plants, the active compound concentration in the use forms is in general between 1 and 0.0001% by weight, preferably between 0.5 and 0.001%. In the treatment of seeds, amounts of active compound of 0.001 to 50 g per kilogram of seed, preferably 0.01 to 10 g are generally required. For the treatment of soil, active compound concentrations of 0.00001 to 0.1% by weight, preferably 0.001 to 0.02%, are required at the place of action.

When the compounds according to the invention are used as plant growth regulators, the amounts applied can be varied within a substantial range. In general, 0.01 to 50 kg, preferably 0.05 to 10 kg, of active compound are used per hectare of soil surface.

When the substances according to the invention are used as plant growth regulators, they are applied within a preferred period of time, the exact definition of which depends on the climatic and vegetative circumstances.

The preparation and use of the active compounds according to the invention can be seen from the following examples.

PREPARATION EXAMPLES

Example 1

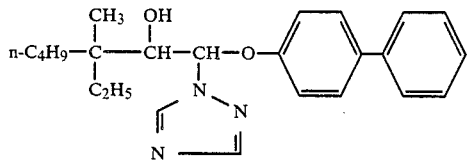

(Process b)

1.5 g (0.04 mole) of sodium boranate are introduced in portions to a solution of 7 g (0.02 mole) of 1-(4-phenyl-phenoxy)-3-ethyl-3-methyl-1-(1,2,4-triazol-1-yl)-heptan-2-one in 70 ml of methanol at 20°–30° C., while stirring. After 2 hours, the solution is brought to pH 6 by addition of acetic acid and evaporated. The residue is taken up in 150 ml of methylene chloride and the solution is washed three times with 250 ml of water each time, dried over sodium sulphate and evaporated in vacuo.

Trituration of the residue with a little diethyl ether gives 3.9 g (56% of theory) of 1-(4-phenylphenoxy)-3-ethyl-3-methyl-1-(1,2,4-triazol-1-yl)-heptan-2-ol (diastereomer mixture) of melting point 120°–122° C.

Example 2

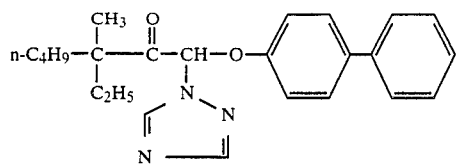

(Process a)

14.5 g (0.21 mole) of 1,2,4-triazole are heated at the boiling point with 29 g (0.07 mole) of 1-bromo-1-(4-phenylphenoxy)-3-ethyl-3-methyl-heptan-2-one in 180 ml of acetonitrile for 10 hours. The reaction mixture is evaporated under reduced pressure, the residue is taken up in 300 ml of methylene chloride and the mixture is washed three times with 400 ml of water each time. After the organic phase has been dried over sodium sulphate, the solvent is distilled off in vacuo and the residue is chromatographed on silica gel with chloroform as the mobile phase.

12 g (44% of theory) of 1-(4-phenylphenoxy)-3-ethyl-3-methyl-1-(1,2,4-triazol-1-yl)-heptan-2-one of melting point 67°–68° C. 3 g (11% of theory) of the isomeric 1-(4-phenyl-phenoxy)-3-ethyl-3-methyl-1-(1,2,4-triazol-4-yl)-heptan-2-one of melting point 154°–155° C. are obtained.

Preparation of the starting substance

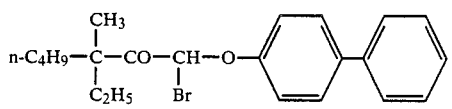

27.5 g (0.172 mole) of bromine are added dropwise to a solution of 56 g (0.172 mole) of 1-(4-phenylphenoxy)-3-ethyl-3-methyl-heptan-2-one in 200 ml of methylene chloride at 20°–30° C. After 15 minutes, 100 ml of an aqueous sodium bisulphite solution are added. The organic phase is separated off, washed three times with 400 ml of water each time, dried over sodium sulphate and evaporated under reduced pressure.

59 g (85% of theory) of crude 1-bromo-1-(4-phenyl-phenoxy)-3-ethyl-3-methyl-heptan-2-one are obtained as a brownish viscous oil.

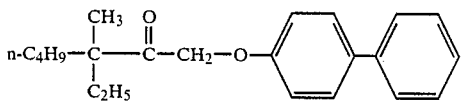

44.2 g (0.26 mole) of 4-hydroxy-biphenyl are heated at the boiling point with 35.9 g (0.26 mole) of potassium carbonate and 50 g (0.26 mole) of 1-chloro-3-ethyl-3-methyl-heptan-2-one in 280 ml of acetone for 10 hours. After the mixture has been cooled to room temperature, it is filtered, the filtrate is evaporated in vacuo and the residue is heated at 200° C. under 0.1 mbar for 1 hour.

56 g (66% of theory) of 1-(4-phenylphenoxy)-3-ethyl-3-methyl-heptan-2-one are obtained as a pale yellowish highly viscous oil.

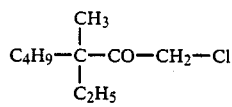

895 g (3.36 moles) of 1-chloro-3-ethyl-3-methyl-2-phenoxy-1-heptene are heated under reflux in 1 liter of ethanol with 500 ml of concentrated hydrochloric acid for 5 hours. The mixture is diluted with methylene chloride and extracted by shaking initially with water and then several times with 2N aqueous sodium hydroxide solution.

After drying and evaporating on a rotary evaporator, 865 g of crude product which, on distillation (boiling point$_{0.3}$ 65° C.), give 520 g (81% of theory) of 1-chloro-3-ethyl-3-methyl-heptan-2-one are obtained.

NMR (CDCl$_3$): δ0.7–1.7 (m, 17H) and 4.3 (s, 2H).

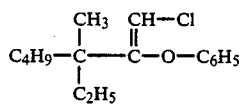

626 g (3 moles) of 1,1-dichloro-3-ethyl-3-methyl-1-heptene and 676 g (6 moles) of sodium phenolate are heated under relfux in 3 l of dimethylformamide for 16 hours. The mixture is diluted with methylene chloride and extracted by shaking several times with 2N aqueous sodium hydroxide solution. After drying and evaporating on a rotary evaporator, 666 g of crude product remain. Distillation at boiling point$_{0.1}$ 100°–110° C. gives 523 g (65% of theory) of 1-chloro-3-ethyl-3-methyl-2-phenoxy-hept-1-ene.

NMR (CDCl$_3$): δ 0.7–1.6 (m, 17H), 5.8 and 5.85 (2 s, 1H) and 6.8–7.4 (m, 5H).

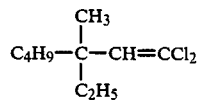

1,235 g (12.7 moles) of 1,1-dichloroethene and 630 g (4.23 moles) of 3-chloro-3-methylheptane are taken at 20° C. 85 g of anhydrous iron(III) chloride are added in portions, while cooling. The mixture is then subsequently stirred at 30° C. for 2 hours. It is poured onto ice and dilute aqueous hydrochloric acid. The organic phase is separated off, dried and subjected to fractional distillation. 627 g (71% of theory) of 1,1-dichloro-3-ethyl-3-methyl-hept-1-ene are isolated at boiling point$_{6.1}$ 50°–60° C.

NMR (CDCl$_3$): δ 0.7–1.8 (m, 17H) and 5.75 and 5.85 (2 s, 1H).

Example 3

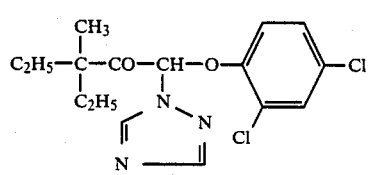

(Process a)

24.2 g (0.351 mole) of 1,2,4-triazole and 43 g (0.117 mole) of 1-bromo-1-(2,4-dichlorophenoxy)-3-ethyl-3-methyl-pentan-2-one in 230 ml of acetonitrile are heated at the boiling point for 10 hours. The mixture is diluted with 300 ml of methylene chloride, the solution is washed three times with 400 ml of water each time and, after drying over sodium sulphate, the solvent is distilled off under reduced pressure. Fractional crystallization of the residue from diethyl ether/petroleum ether (1:1) gives: 24 g (58% of theory) of 1-(2,4-dichlorophenoxy)-3-ethyl-3-methyl-1-(1,2,4-triazol-1-yl)-pentan-2-one of melting point 68°–69° C. and 7.3 g (17.5% of theory) of the isomeric 1-(2,4-dichlorophenoxy)-3-ethyl-3-methyl-1-(1,2,4-triazol-1-yl)-pentan-2-one of melting point 154°–155° C.

Preparation of the precursor

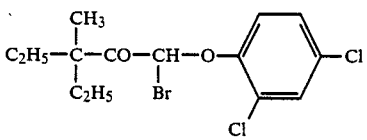

38.4 g (0.24 mole) of bromine are added dropwise to a solution of 75.7 g (0.238 mole) of 1-(2,4-dichlorophenoxy)-3-ethyl-3-methyl-pentan-2-one in 300 ml of methylene chloride, while stirring. After 15 minutes, 100 ml of aqueous sodium bisulphite solution are added. The organic phase is separated off, washed three times with 400 ml of water and, after drying over sodium sulphate, evaporated in vacuo.

87 g (99% of theory) of crude 1-bromo-1-(2,4-dichlorophenoxy)-3-ethyl-3-methyl-pentan-2-one are obtained as a brownish liquid which is subsequently reacted without further purification.

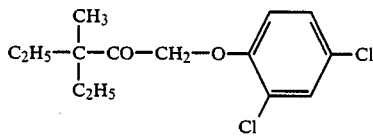

50 g (0.28 mole) of 1-chloro-3-ethyl-3-methyl-pentan-2-one, dissolved in 30 ml of N,N-dimethylformamide, are added to a mixture of 38.6 g (0.28 mole) of potassium carbonate and 45.6 g (0.28 mole) of 2,4-dichlorophenol in 200 ml of N,N-dimethylformamide at the boiling point. The mixture is heated at the boiling point for 10 hours, cooled to room temperature and filtered and the solvent is distilled off under reduced pressure. Distillation of the residue gives 75.7 g (93.5% of theory) of 1-(2,4-dichlorophenoxy)-3-ethyl-3-methyl-pentan-2-one as a color less liquid of boiling point 141°–144° C./0.15 mm.

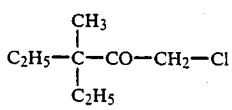

1,522 g (6.38 moles) of 1-chloro-3-ethyl-3-methyl-2-phenoxy-1-pent-1-ene are stirred in 3.4 l of formic acid at 60° C. for 5 hours, with the addition of concentrated hydrochloric acid. The mixture is diluted with methylene chloride and then washed with water and subsequently extracted several times by shaking with 2N aqueous sodium hydroxide solution. After drying and stripping off the solvent, 927 g of crude product remain. Distillation at boiling point$_{0.2}$ 62°–70° C. gives 878 g (85% of theory) of 1-chloro-3-ethyl-3-methyl-pentan-2-one.

NMR (CDCl$_3$): δ 0.8 (t, 6H), 1.15 (s, 3H), 1.6 (q, 4H) and 4.3 (s, 2H).

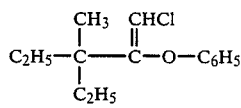

1,786 g (8.23 moles) of 3-ethyl-3-methyl-1,1,1-trichloropentane are added dropwise to a mixture of 2,030 g (17.5 moles) of sodium phenolate and 1,173 g (8.5 moles) of potassium carbonate in 4 l of N-methylpyrrolidone at 195°–200° C. The mixture is subsequently stirred at 200° C. for 8 hours. After dilution with methylene chloride, it is extracted several times by shaking with water and 2N aqueous sodium hydroxide solution.

Distillation of the crude product (2,470 g) gives 1,507 g (77% of theory) of 1-chloro-3-ethyl-3-methyl-2-phenoxy-pent-1-ene.

NMR (CDCl$_3$): δ 0.7–1.7 (m, 13H), 5.8 (s, 1H), 6.8–7.5 (m, 5H).

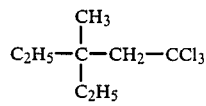

2,328 g (24 moles) of 1,1-dichloroethene are taken at −75° C. 80 g of powdered aluminum chloride are added, and 964 g (8 moles) of 3-chloro-3-methylpentane are added dropwise in the course of 4 hours. The mixture is subsequently stirred at −70° C. for 2 hours and poured onto ice and dilute hydrochloric acid. Extraction with methylene chloride gives 1,659 g of crude product, which is purified by distillation at boiling point$_{20}$ 95°–110° C.

1,495 g (86% of theory) of 3-ethyl-3-methyl-1,1,1-trichloropentane are obtained.

NMR (CDCl$_3$): δ 0.8 (t, 6H), 1.15 (s, 3H), 1.55 (q, 4H) and 2.8 (s, 2H).

Example 4

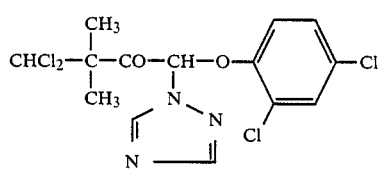

(Process a)

27.8 g (0.067 mole) of 1-bromo-4,4-dichloro-1-(2,4-dichlorophenoxy)-3,3-dimethyl-butan-2-one, dissolved in 30 ml of acetonitrile, are added to a boiling solution of 13.9 g (0.2 mole) of 1,2,4-triazole in 150 ml of acetonitrile. The solution is heated at the boiling point for eight hours, cooled to 20° C. and diluted with 300 ml of methylene chloride. It is then washed three times with 300 ml of water each time, the organic phase is dried over sodium sulphate and concentrated in vacuo and the residue is filtered over silica gel with chloroform as the eluent.

13 g (49% of theory) of 4,4-dichloro-1-(2,4-di-chlorophenoxy)-3,3-dimethyl-1-(1,2,4-triazol-1-yl)-butan-2-one are obtained as colorless crystals of melting point 120°–121° C.

Further elution with ethyl acetate gives 5 g (19% of theory) of the isomeric 4,4-dichloro-1-(2,4-di-chlorophenoxy)-3,3-dimethyl-1-(1,2,4-triazol-1-yl)-butan-2-one in the form of colorless crystals of melting point 177°–178° C.

Example 5

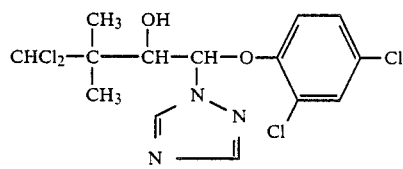

(Process b)

1.5 g (0.04 mole) of sodium boranate are added in portions to a solution of 8 g (0.02 mole) of 4,4-dichloro-1-(2,4-dichlorophenoxy)-3,3-dimethyl-1-(1,2,4-triazol-1-yl)-butan-2-one in 80 ml of methanol at 20°–30° C., while stirring. After two hours, the mixture is brought to pH 6 by addition of acetic acid. The solution is evaporated under reduced pressure, the residue is taken up in 200 ml of methylene chloride and the mixture is washed three times with 400 ml of water each time and dried over sodium sulphate. After evaporating the solution and removing the residual solvent by warming the residue at 50° C. under 0.01 bar for two hours, 6 g (75% of theory) of 4,4-dichloro-1-(2,4-dichlorophenoxy)-3,3-dimethyl-1-(1,2,4-triazol-1-yl)-butan-2-ol are obtained as a 3:1 mixture of the two diastereomers in the form of a highly viscous oil.

Example 6

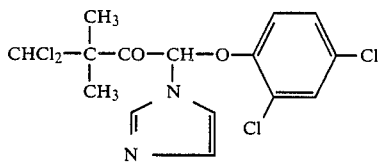

(Process a)

10.2 g (0.15 mole) of imidazole and 24 g (0.05 mole) of 1-bromo-4,4-dichloro-1-(2,4-dichlorophenoxy)-3,3-dimethyl-butan-2-one in 230 ml of acetonitrile are heated at the boiling point for eight hours. After cooling to room temperature, the mixture is diluted with 200 ml of methylene chloride and the solution is washed three times with 400 ml of water each time. After drying the organic phase over sodium sulphate, it is evaporated in vacuo and the residue is filtered over silica gel with chloroform as the mobile phase.

17 g (86% of theory) of 4,4-dichloro-1-(2,4-dichlorophenoxy)-3,3-dimethyl-1-(imidazol-1-yl)-butan-2-one are obtained as colorless crystals of melting point 125°–126° C.

The compounds of the general formula

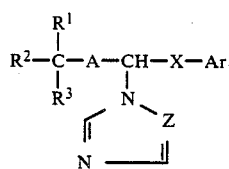

listed by way of their formulae in the following table are obtained in a corresponding manner by processes analogous to those described:

| Example No. | R¹ | R² | R³ | A | Z | X | Ar | Physical data |
|---|---|---|---|---|---|---|---|---|
| 7 | CHCl₂ | CH₃ | CH₃ | CHOH | CH | O | 2,4-Cl₂-C₆H₃ | Resin* |
| 8 | CHCl₂ | CH₃ | CH₃ | CO | N | O | 4-Cl-C₆H₄ | Melting point 59–60° C. |
| 9 | CHCl₂ | CH₃ | CH₃ | CHOH | N | O | 4-Cl-C₆H₄ | Melting point 129–135° C. |
| 10 | CHCl₂ | CH₃ | CH₃ | CO | CH | O | 4-Cl-C₆H₄ | $n_D^{25}$: 1,555 |
| 11 | CHCl₂ | CH₃ | CH₃ | CHOH | CH | O | 4-Cl-C₆H₄ | Melting point 90–134° C. |
| 12 | CHCl₂ | CH₃ | CH₃ | CO | N | O | 4-biphenylyl | Melting point 177–178° C. |
| 13 | CHCl₂ | CH₃ | CH₃ | CO | CH | O | 4-biphenylyl | Resin |
| 14 | n-C₄H₉ | C₂H₅ | CH₃ | CO | N | O | 2,4-Cl₂-C₆H₃ | Resin |
| 15 | n-C₄H₉ | C₂H₅ | CH₃ | CO | CH | O | 2,4-Cl₂-C₆H₃ | Resin |
| 16 | n-C₄H₉ | C₂H₅ | CH₃ | CHOH | N | O | 2,4-Cl₂-C₆H₃ | Resin* |
| 17 | n-C₄H₉ | C₂H₅ | CH₃ | CHOH | CH | O | 2,4-Cl₂-C₆H₃ | Resin* |

-continued

| Example No. | R¹ | R² | R³ | A | Z | X | Ar | Physical data |
|---|---|---|---|---|---|---|---|---|
| 18 | n-C₄H₉ | C₂H₅ | CH₃ | CO | N | O | 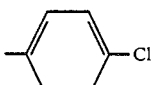 | Resin |
| 19 | n-C₄H₉ | C₂H₅ | CH₃ | CHOH | N | O | 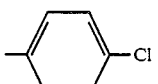 | Resin* |
| 20 | n-C₄H₉ | C₂H₅ | CH₃ | CO | N | O | 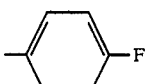 | Resin |
| 21 | n-C₄H₉ | C₂H₅ | CH₃ | CO | CH | O | 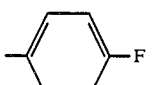 | Resin |
| 22 | n-C₄H₉ | C₂H₅ | CH₃ | CHOH | N | O | 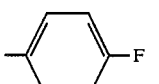 | Resin* |
| 23 | n-C₄H₉ | C₂H₅ | CH₃ | CHOH | CH | O | 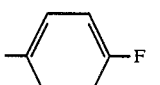 | Resin* |
| 24 | n-C₄H₉ | C₂H₅ | CH₃ | CO | CH | O | 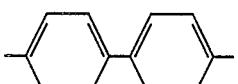 | Resin |
| 25 | n-C₄H₉ | C₂H₅ | CH₃ | CHOH | CH | O | 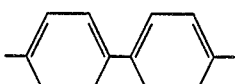 | Viscous oil* |
| 26 | C₂H₅ | C₂H₅ | CH₃ | CHOH | N | O | 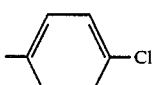 | Viscous oil* |
| 27 | C₂H₅ | C₂H₅ | CH₃ | CO | CH | O | 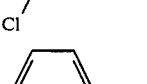 | Viscous oil |
| 28 | C₂H₅ | C₂H₅ | CH₃ | CHOH | CH | O | 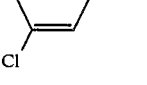 | Viscous oil |
| 29 | C₂H₅ | C₂H₅ | CH₃ | CO | N | O | 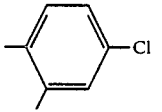 | Viscous oil |
| 30 | C₂H₅ | C₂H₅ | CH₃ | CO | CH | O | 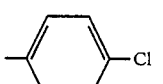 | Viscous oil |
| 31 | C₂H₅ | C₂H₅ | CH₃ | CHOH | N | O | 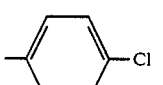 | Viscous oil |
| 32 | C₂H₅ | C₂H₅ | CH₃ | CHOH | CH | O | 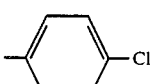 | Melting point 134–136° C.* |

-continued

| Example No. | R¹ | R² | R³ | A | Z | X | Ar | Physical data |
|---|---|---|---|---|---|---|---|---|
| 33 | n-$C_4H_9$ | $C_2H_5$ | $CH_3$ | CO | CH | O | 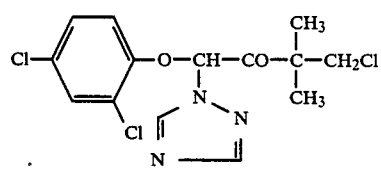 | Resin |
| 34 | $CHCl_2$ | $CH_3$ | $CH_3$ | CHOH | N | O | 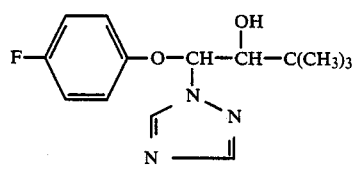 | Melting point 123–125° C. |
| 35 | n-$C_4H_9$ | $C_2H_5$ | $CH_3$ | CHOH | CH | O | 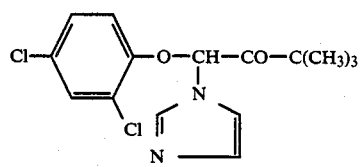 | Resin* |
| 36 | $CHCl_2$ | $CH_3$ | $CH_3$ | CHOH | N | O | 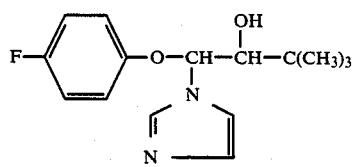 | Melting point 149–151° C. pure diastereomer |

*Diastereomer mixture

Use Examples

The substances shown below are employed as the comparison substances in the following use examples:

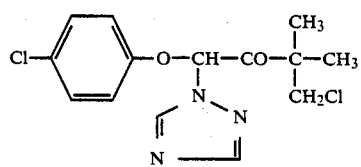 (A)

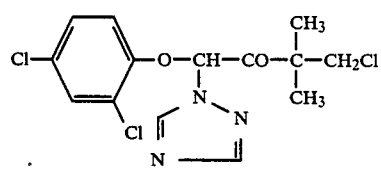 (B)

(Note: images B–E, F–J follow)

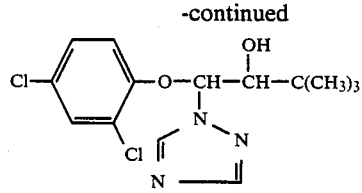 (F)

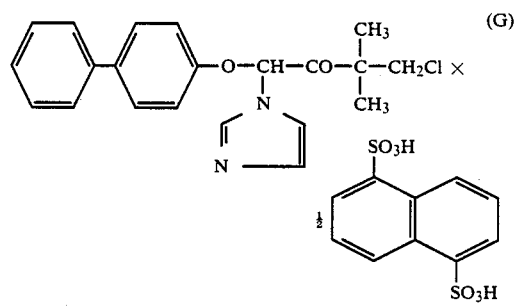 (G)

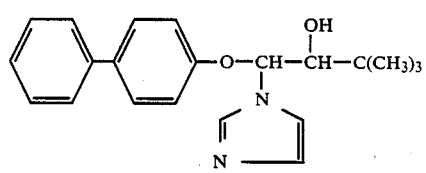 (H)

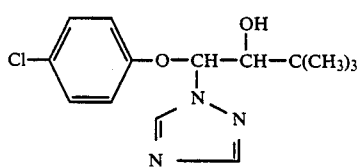 (J)

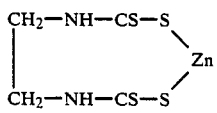 (K)

Example A

Puccinia test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita with in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, the substances according to the invention which are described in Examples 8 and 12 show a clearly better activity than comparison substance (A).

Example B

*Leptosphaeria nodorum* test (wheat)/protective

Solvent: 100 parts by weight of dimethylformamide
Emulsifiers: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, the substances according to the invention which are described in Examples 19, 34 and 36 show a clearly better activity than comparison substance (B). The substances according to the invention which are described in Examples 13, 15 and 33 furthermore show a clearly better activity than comparison substance (C). Finally, the substance according to the invention which is described in Example 27 shows a clearly better activity than comparison substance (D).

Example C

Uromyces test (dwarf bean)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus) and remain in a dark humidity chamber at 20° to 22° C. and 100% relative atmospheric humidity for 1 day.

The plants are then placed in a greenhouse under intensive illumination at 20° to 22° C. and a relative atmospheric humidity of 70 to 80% for 9 days.

Evaluation is carried out 10 days after the inoculation.

In this test, the substances according to the invention which are described in Examples 8 and 12 show a clearly better activity than comparison substance (E). The substances according to the invention which are described in Examples 1, 9, 19, 31 and 34 furthermore show a clearly better activity than the comparison substance.

Example D

Venturia test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, the substances according to the invention which are described in Examples 15 and 21 show a clearly better activity than comparison substance (G).

Example E

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus Sphaerotheca fuliginea.

The plants are then placed in a greenhouse at 23° to 24° C. and at a relative atmospheric humidity of about 75%.

Evaluation is carried out 10 days after the inoculation.

In this test, the substances according to the invention which are described in Examples 23, 25, 28, 32 and 35 show a clearly better activity than comparison substance (H).

Example F

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amounts of solvent, and the concentrate is diluted with water and the stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the substances according to the invention which are described in Examples 9, 16, 31 and 34 show a clearly better activity than comparison substance (J).

The substances according to the invention which are described in Examples 13, 15, 21, 24, 30 and 33 furthermore show a clearly better activity than comparison substance (K).

Example G

Growth of cotton

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. At this stage, the plants are sprayed with the preparations of active compound until dripping wet. After 3 weeks the additional growth of all the plants is measured and is calculated as a percentage of the additional growth of the controls. 100% denotes an additional growth as in the controls, values below 100% indicate growth inhibition and values above 100% indicate promotion of growth.

In this test, the substance according to the invention which is described in Example 16 shows a very potent growth-inhibiting action.

Example H

Growth of sugar beet

Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Sugar beet is grown in a greenhouse until formation of the cotyledons is complete. At this stage, the plants are sprayed with the preparation of active compound until dripping wet. After 14 days, the additional growth of the plants is measured and is calculated as a percentage of the additional growth of the control plants. 100% denotes an additional growth as in the controls, values below 100% indicate growth inhibition and values above 100% indicate promotion of growth.

In this test, the substances according to the invention which are described in Examples 9 and 16 show a very potent growth-inhibiting action.

It is understood that the specification and examples are illustrative but not limitative of the present invention and that other embodiments within the spirit and scope of the invention will suggest themselves to those skilled in the are.

We claim:

1. An azolyl ether ketone or alcohol of the formula $$CHCl_2-\underset{\underset{CH_3}{|}}{\overset{\overset{CH_3}{|}}{C}}-A-\underset{\underset{N\diagdown_N}{\overset{|}{\underset{\parallel}{N}}}}{\overset{|}{CH}}-O-Ar$$

in which
A represents the keto group or a CH(OH) grouping, and
Ar represents phenyl which is optionally mono- or di-substituted by identical or different substituents selected from the group consisting of fluorine, chlorine and phenyl, or an addition product thereof with an acid or metal salt.

2. A ketone or addition product thereof according to claim 1, wherein such compound is 4,4-dichloro-1-(2,4-dichlorophenoxy)-3,3-dimethyl-1-(1,2,4-triazol-1-yl)butan-2-one of the formula $$CHCl_2-\underset{\underset{CH_3}{|}}{\overset{\overset{CH_3}{|}}{C}}-CO-\underset{\underset{N\diagdown_N}{\overset{|}{\underset{\parallel}{N}}}}{\overset{|}{CH}}-O-\underset{Cl}{\underset{|}{\bigcirc}}-Cl$$

or an addition product thereof with an acid or metal salt.

3. An alcohol or addition product thereof according to claim 1, wherein such compound is 4,4-dichloro-1-(2,4-dichlorophenoxy)-3,3-dimethyl-1-(1,2,4-triazol-1-yl)-butan-2-ol of the formula

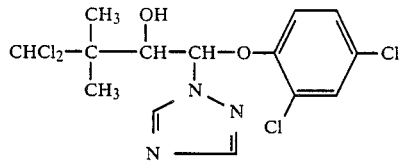

or an addition product thereof with an acid or metal salt.

4. A fungicidal and plant-growth regulating composition comprising a fungicidally and plant-growth regulating effective amount of an azolyl ketone, alcohol or addition product thereof according to claim 1 and an insert diluent.

5. A method of combating fungi which comprises applying to such fungi or to a fungus habitat a fungicidally effective amount of a ketone, alcohol or addition product thereof according to claim 1.

6. The method according to claim 5, wherein such compound is
4,4-dichloro-1-(2,4-dichlorophenoxy)-3,3-dimethyl-1-(1,2,4-triazol-1-yl-butan-2-one, or
4,4-dichloro-1-(2,4-dichlorophenoxy)-3,3-dimethyl-1-yl)-butan-2-ol,
or an addition product thereof with an acid or metal salt.

7. A method of regulating the growth of plants which comprises applying to such plants or to a locus in which plants are grown or to be grown a plant-growth regulating effective amount of a ketone, alcohol or addition product thereof according to claim 1.

8. The method according to claim 7, wherein such compound is
4,4-dichloro-1-(2,4-dichlorophenoxy)-3,3-dimethyl-1-(1,2,4-triazol-1-yl-butan-2-one, or
4,4-dichloro-1-(2,4-dichlorophenoxy)-3,3-dimethyl-1-yl)-butan-2-ol,
or an addition product thereof with an acid or metal salt.

* * * * *